United States Patent [19]

Ehrenfreund

[11] 4,162,330
[45] Jul. 24, 1979

[54] ACYLUREA INSECTICIDES

[75] Inventor: Josef Ehrenfreund, Allschwil, Switzerland

[73] Assignee: Ciba-Geigy Corporation, Ardsley, N.Y.

[21] Appl. No.: 927,444

[22] Filed: Jul. 24, 1978

[30] Foreign Application Priority Data

Jul. 28, 1977 [CH] Switzerland .......................... 9349/77
Jun. 29, 1978 [CH] Switzerland .......................... 7101/78

[51] Int. Cl.$^2$ ........................ C07C 127/22; A01N 9/12
[52] U.S. Cl. .................................. 424/322; 260/553 E
[58] Field of Search ...................... 260/553 E; 424/322

[56] References Cited

U.S. PATENT DOCUMENTS

| | | | |
|---|---|---|---|
| 3,384,473 | 5/1968 | Pillon et al. | 260/553 E X |
| 3,406,192 | 10/1968 | Speziale et al. | 260/553 E X |
| 3,989,842 | 11/1976 | Wellinga et al. | 260/553 E X |
| 3,992,553 | 11/1976 | Sirrenberg et al. | 260/553 E X |
| 4,005,223 | 1/1977 | Sirrenberg et al. | 260/553 E X |
| 4,013,717 | 3/1977 | Wellinga et al. | 260/553 E |
| 4,041,177 | 8/1977 | Sirrenberg et al. | 260/553 E X |
| 4,068,002 | 1/1978 | Sirrenberg et al. | 260/553 E X |
| 4,085,226 | 4/1978 | Sirrenberg et al. | 260/553 E X |
| 4,089,975 | 5/1978 | Wade et al. | 260/553 E X |

FOREIGN PATENT DOCUMENTS 1568641 4/1970 Fed. Rep. of Germany ...... 260/553 A
2601780 7/1977 Fed. Rep. of Germany ...... 260/553 E Primary Examiner—Thomas Waltz
Attorney, Agent, or Firm—Frederick H. Rabin

[57] ABSTRACT

Novel N-phenyl-N'-benzoylureas of the formula

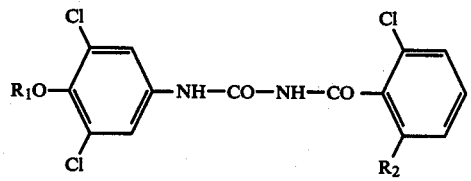

wherein $R_1$ represents $CH_2=CH-CH_2-$, $CHCl=CCl-$, $CHCl=CH-CH_2-$, $CH_2=CCl-CH_2-$, $CCl_2=CH-CH_2-$, $CHCl=CCl-CH_2-$ or $CH\equiv C-CH_2-$, and $R_2$ represents hydrogen or chlorine; processes for producing these compounds; and also compositions containing these compounds for use in combating pests, particularly for combating insect pests in the fields of plant protection and hygiene.

9 Claims, No Drawings

ACYLUREA INSECTICIDES

The present invention relates to novel N-phenyl-N'-benzoylureas, to processes for producing them and to their use for combating pests.

These novel N-phenyl-N'-benzoylureas have the formula I

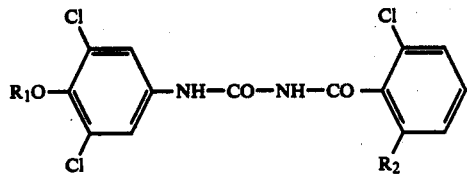

wherein $R_1$ — represents $CH_2=CH-CH_2-$, $CHCl=CCl-$, $CHCl=CH-CH_2-$, $CH_2=CCl-CH_2-$, $CCl_2=CH-CH_2-$, $CHCl=CCl-CH_2-$ or $CH\equiv C-CH_2-$, and $R_2$ — represents hydrogen or chlorine.

A preferred group of compounds of the formula I is that wherein $R_2$ represents hydrogen.

Compounds of the formula I to be emphasised by virtue of their effectiveness, especially against pests in the field of hygiene, are also those in which $R_1$ represents the $CH_2=CH-CH_2-$, $CHCl=CCl-$ or $CHCl=CH-CH_2$ radical.

The compounds of the formula I according to the invention can be produced by processes known per se, for example by reaction (a) of a compound of the formula II

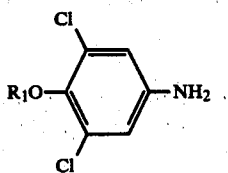

with a compound of the formula III

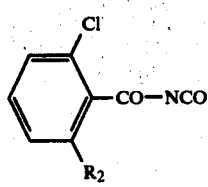

(b) of a compound of the formula IV

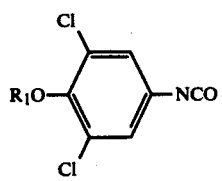

with a compound of the formula V

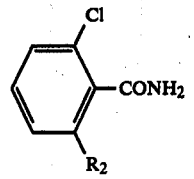

In the above formulae II to V, $R_1$ and $R_2$ have the meanings given under the formula I.

The processes a) and b) given above can be performed under normal or elevated pressure, and preferably in the presence of an organic solvent or diluent. Suitable solvents or diluents are, for example, ethers and ethereal compounds such as diethyl ether, dipropyl ether, dibutyl ether, dioxane, dimethoxyethane and tetrahydrofuran; N,N-dialkylated carboxylic acid amides; aliphatic, aromatic and also halogenated hydrocarbons, particularly benzene, toluene, xylene, chloroform, methylene chloride, carbon tetrachloride and chlorobenzene; nitriles such as acetonitrile or propionitrile; dimethylsulphoxide, as well as ketones, for example acetone, methyl ethyl ketone, methylisopropyl ketone and methylisobutyl ketone. Process a) can be performed at a temperature of $-10°$ to $+100°$ C., preferably between 15 and 25° C., optionally in the presence of a basic substance, for example an organic base, such as triethylamine. Process b) is performed generally at a temperature of 0° to 120° C., preferably at the boiling point of the solvent used, and in the presence of an organic base, such as pyridine, and/or with the addition of an alkali metal or alkaline-earth metal, preferably sodium.

The compounds of the formula I are obtained — where this is at all possible — as cis/trans isomeric mixtures. In this respect, the term 'compounds of the formula I' is to be understood as embracing both the cis and trans forms, and the corresponding isomeric mixtures. An isomeric mixture can be separated, for example, by means of the known chromatographical methods of separation and subsequent elution into the isomeric forms. A further chromatographical separating method is gas-chromatography. In certain cases, isomeric separation can also be performed by fractional crystallisation.

Some of the starting materials of the formulae II, III, IV and V are known and can be produced by processes analogous to known processes. The anilines of the formula II are obtainable by application of the procedures described in Chem. Ber. 34, 1940 Ann. 418, 109. The conversion of these anilines into isocyanates of the formula IV can be effected with phosgene by processes commonly in use. The benzoylisocyanates of the formula III and processes for producing them are known from the German Offenlegungsschrift No. 2,123,236 (see also J. Org. Chem. 30, 4306; 1965). The production of the benzamides of the formula V is described in Beilstein "Handbuch der organischen Chemie," Vol. 9, 336.

The compounds of the formula I have a broad biocidal action and are suitable for combating various insect pests which infest plants and animals. Furthermore, the compounds of the formula I are distinguished by their anti-feeding action on insects which damage plants by eating. The compounds of the formula I are particularly suitable for controlling insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tipulidae, Stomoxydae, Muscidae, Calliphoridae, Trypetidae and Pulicidae.

In addition to having a favourable action against flies, such as Musca domestica, and mosquitoes, the compounds of the formula I also have a favourable action against insects that damage plants, especially insects that damage plants by eating, in crops of ornamental plants and useful plants, particularly in cotton crops (e.g. against Spodoptera littoralis and Heliothis virescens) and in crops of vegetables (e.g. against Leptinotarsa decemlineata and Myzus persicae).

The insecticidal action can be substantially broadened and adapted to suit given circumstances by the addition of other insecticides and/or acaricides. Suitable additives are, for example, organic phosphorus compounds; nitrophenols and derivatives thereof; formamidines; ureas; pyrethrin-like compounds as well as carbamates and chlorinated hydrocarbons.

Compounds of the formula I can be combined particularly advantageously also with substances which have the effect of intensifying the action of the compounds. Examples of such substances are, inter alia: piperonylbutoxide, propynyl ethers, propynyl oximes, propynyl carbamates and propynyl phosphonates, 2-(3,4-methylenedioxyphenoxy)-3,6,9-trioxaundecane and S,S,S-tributylphosphorotrithioates.

The compounds of the formula I can be used on their own or together with suitable carriers and/or additives. Suitable carriers and additives may be solid or liquid, and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:
solid preparations: dusts, scattering agents or granulates (coated granules, impregnated granules and homogeneous granules);
liquid preparations:
 (a) water-dispersible concentrates of active substance: wettable powders, pastes or emulsions;
 (b) solutions.

The content of active substance in the described compositions is between 0.1 and 95%.

The active substances of the formula I can be formulated, for example, as follows:

Dusts

The following substances are used to produce a) a 5% dust and b) a 2% dust:
(a)—5—parts of active substance, and
  95—parts of talcum;
(b)—2—parts of active substance,
  1—part of highly dispersed silicic acid, and
  97—parts of talcum.

The active substance is mixed and ground with the carriers.

Granulate

The following ingredients are used to produce a 5% granulate:
5—parts of active substance
0.25—part of epichlorohydrin,
0.25—part of cetyl polyglycol ether,
3.50—parts of polyethylene glycol, and
91—parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin and the acetone is subsequently evaporated off in vacuo.

Wettable powders

The following constituents are used to produce a) a 40%, b) and c) a 25% and d) a 10% wettable powder:
(a)—40—parts of active substance,
  5—parts of sodium lignin sulphonate,
  1—part of sodium dibutyl-naphthalene sulphonate, and
  54—parts of silica acid;
(b)—25—parts of active substance,
  4.5—parts of calcium lignin sulphonate,
  1.9—parts of Champagne chalk/hydroxyethyl cellulose mixture (1:1),
  1.5—parts of sodium dibutyl-naphthalene sulphonate,
  19.5—parts of silicic acid,
  19.5—parts of Champagne chalk, and
  28.1—parts of kaolin;
(c)—25—parts of active substance,
  2.5—parts of isooctylphenoxy-polyoxyethylene-ethanol,
  1.7—parts of Champagne chalk/hydroxyethyl cellulose mixture (1:1),
  8.3—parts of sodium aluminium silicate,
  16.5—parts of kieselgur, and
  46—parts of kaolin;
(d)—10—parts of active substance,
  3—parts of a mixture of the sodium salts of saturated fatty alcohol sulphates,
  5—parts of naphthalenesulphonic acid/formaldehyde condensate, and
  82—parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce a) a 10% b) a 25% and c) a 50% emulsifiable concentrate:
(a)—10—parts of active substance,
  3.4—parts of epoxidised vegetable oil,
  3.4—parts of a combination emulsifier consisting of fatty alcohol polyglycol ether and alkylarylsulphonate calcium salt,
  40—parts of dimethylformamide, and
  43.2—parts of xylene;
(b)—25—parts of active substance, 2.5—parts of epoxidised vegetable oil,
10—parts of an alkylarylsulphonate/fatty alcohol polyglycol ether mixture,
5—parts of dimethylformamide, and
57.5—parts of xylene;
(c)—50—parts of active substance,
4.2—parts of tributylphenol-polyglycol ether,
5.8—parts of calcium-dodecylbenzenesulphonate,
20—parts of cyclohexanone, and
20—parts of xylene.

Emulsions of the concentration required can be prepared from these concentrates by dilution with water.

Spray

The following constituents are used to produce a) a 5% spray and b) a 95% spray:
(a)—5—parts of active substance,
1—part of epichlorohydrin, and
94—parts of ligroin (boiling limites 160°–190° C.);
(b)—95—parts of active substance, and
5—parts of epichlorohydrin.

The invention is further illustrated by the following Examples.

EXAMPLE 1

Production of N-3,5-dichloro-4-allyloxyphenyl-N'-2,6-dichlorobenzoylurea 3.5 g of 2,6-dichlorobenzoylisocyanate in 10 ml of absolute ether is added dropwise, at room temperature, to a solution of 3.3 g of 3,5-dichloro-4-allyloxyaniline in 50 ml of absolute ether. The precipitate separating out after a short time is filtered off with suction, and washed with ether to thus yield the title compound of the formula

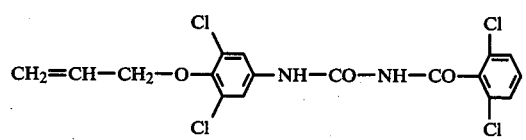

having a melting point of 210°–211° C.

The following compounds are produced in an analogous manner:

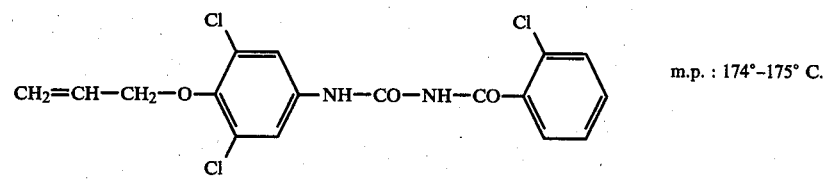

m.p. : 174°–175° C.

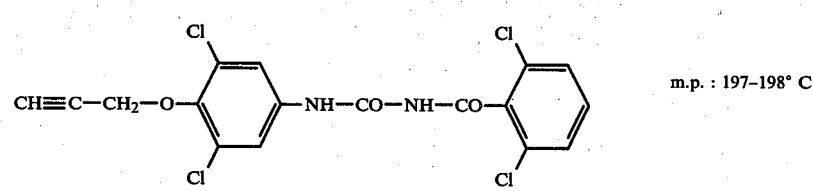

m.p. : 197–198° C

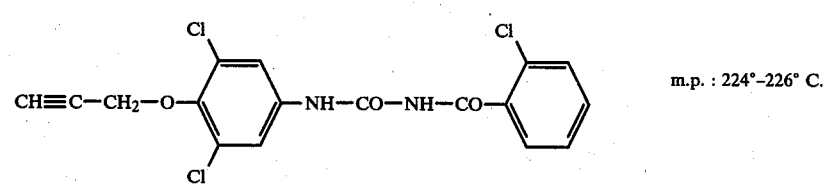

m.p. : 224°–226° C.

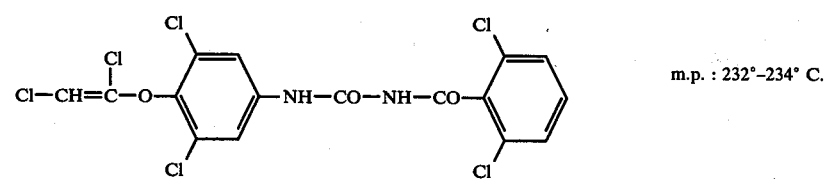

m.p. : 232°–234° C.

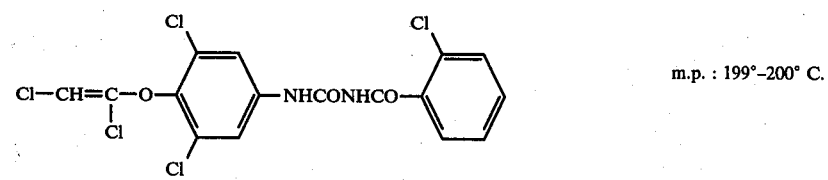

m.p. : 199°–200° C.

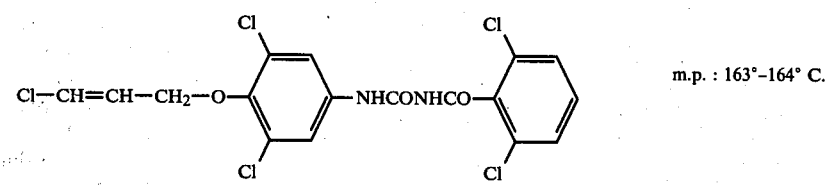

m.p. : 163°–164° C.

-continued

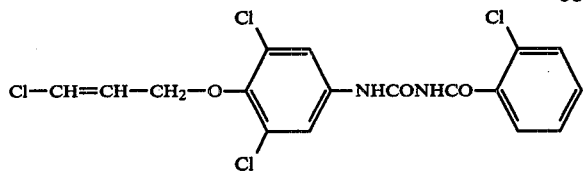

m.p.: 172°–173° C.

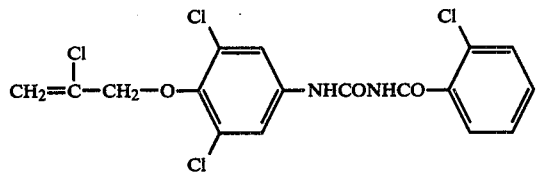

m.p.: 195°–196° C.

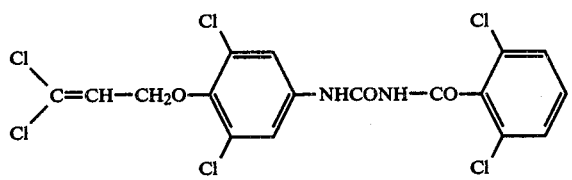

m.p.: 171°–172° C.

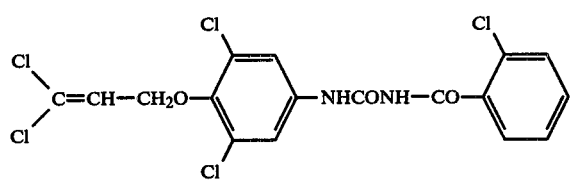

m.p.: 201°–203° C.

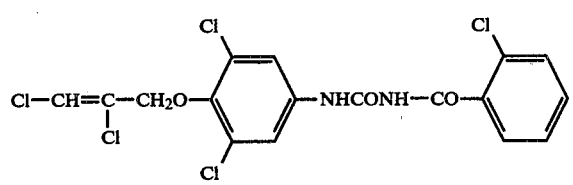

m.p.: 202°–205° C.

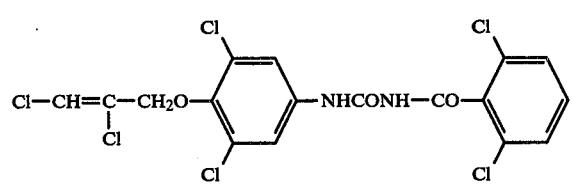

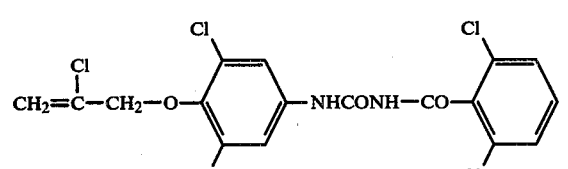

EXAMPLE 2

Action against Musca domestica

An amount of 50 g of maggot substrate was weighed off into each beaker. 2.5 ml of a 1% acetonic solution of each active substance was transferred by pipette twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of ten days, the number of emerged flies were determined and hence any effect on metamorphosis was established. Compounds according to Example 1 exhibited in this test a good action against Musca domestica.

EXAMPLE 3

Action against Lucilia sericata 1 ml of an aqueous solution containing 0.5% of active substance was placed onto 9 ml of a culture medium at 50° C. About 30 freshly emerged Lucilia sericata larvae were then transferred to the culture medium, and after 48 and 96 hours, respectively, the insecticidal action was determined by ascertaining the mortality rate.

Compounds according to Example 1 exhibited in this test a good action against Lucilia sericata.

EXAMPLE 4

Action against Aëdes aegypti

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 two-day-old Aëdes larvae were placed into each container. The mortality rate was ascertained after 1, 2 and 5 days.

Compounds according to Example 1 exhibited in this test a good action against Aëdes aegypti.

EXAMPLE 5

Insecticidal stomach poison action

Cotton plants were sprayed with a 0.05% aqueous emulsion of the active substance (obtained from a 10% emulsifiable concentrate).

After drying of the coating obtained, Spodoptera littoralis larvae and Heliothis virescens larvae L₃, respectively, were placed onto the cotton plants. The test was carried out at 24° C. with 60% relative humidity.

Compounds according to Example 1 exhibited in the above test a good insecticidal stomach poison action against the larvae of Spodoptera littoralis and Heliothis virescens.

I claim:

1. N-Phenyl-N'-benzoylurea of the formula I

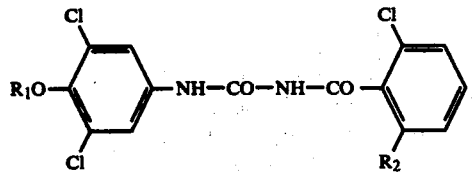

wherein
R₁—represents CH₂═CH—CH₂—, CHCl═CCl—, CHCl═CH—CH₂—, CH₂═CCl—CH₂—, CCl₂═CH—CH₂—, CHCl═CCl—CH₂— or CH≡C—CH₂—, and
R₂—represents hydrogen or chlorine.

2. A compound according to claim 1 of the formula I, wherein R₂ represents hydrogen.

3. A compound according to claim 1 of the formula I, wherein R₁ represents CH₂═CH—CH₂—, CHCl═CCl— or CHCl═CH—CH₂—.

4. A compound according to claim 2, wherein R₂ represents hydrogen.

5. A compound according to claim 4 of the formula

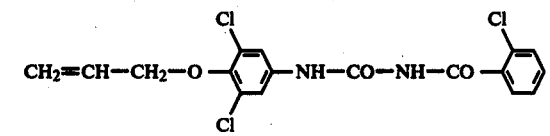

6. A compound according to claim 4 of the formula

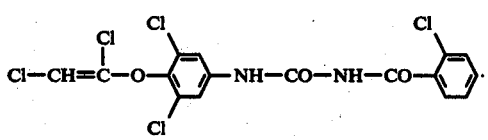

7. A compound according to claim 4 of the formula

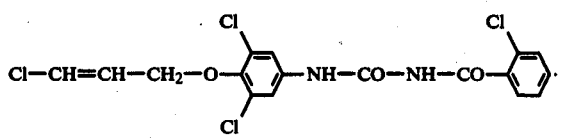

8. An insecticidal composition which comprises an insecticidally effective amount of a compound of the formula I according to any one of claims 1 to 7, and suitable carriers or other additives.

9. A method of combating insects which comprises applying an insecticidally effective amount of a compound of the formula I according to any one of claims 1 to 7 to said insects.

* * * * *